United States Patent [19]

Rheinheimer et al.

[11] Patent Number: 5,006,155
[45] Date of Patent: Apr. 9, 1991

[54] PYRIDINE DERIVATIVES AND THEIR USE AS HERBICIDES

[76] Inventors: Joachim Rheinheimer, 24 Merziger Strasse, 6700 Ludwigshafen; Karl Eicken, 12 Am Huettenwingert, 6706 Wachenheim; Peter Plath, 13 Hans-Blacke-Strasse, 6710 Frankenthal; Karl-Otto Westphalen, 58 Mausbergweg, 6720 Speyer; Bruno Wuerzer, 13 Ruedigerstrasse, 6701 Otterstadt, all of Fed. Rep. of Germany

[21] Appl. No.: 435,671

[22] Filed: Nov. 14, 1989

[30] Foreign Application Priority Data

Dec. 9, 1988 [DE] Fed. Rep. of Germany ....... 3841432

[51] Int. Cl.$^5$ .................. C07D 239/34; C07D 251/26; C07D 401/12; A01N 43/66
[52] U.S. Cl. .......................................... 71/92; 71/93; 544/218; 544/300; 544/310; 544/316
[58] Field of Search ............... 544/218, 310, 300, 316; 71/92, 93

[56] References Cited
FOREIGN PATENT DOCUMENTS
0249707 12/1987 European Pat. Off. ............ 544/310

OTHER PUBLICATIONS
Chemical Abstracts, vol. 112 (15), Abst. No. 139,041-p, Apr. 9, 1990, abstracting Eur. Pat. Appl. EP-335,409, pub. Oct. 4, 1989.

Primary Examiner—Alan L. Rotman
Attorney, Agent, or Firm—Keil & Weinkauf

[57] ABSTRACT

Pyridine derivatives of the formula

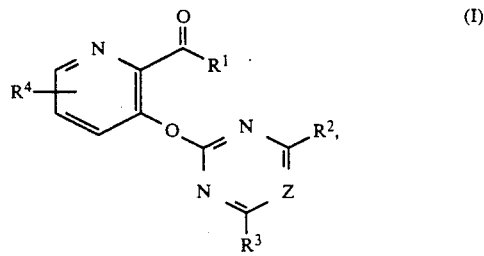

where $R^1$ is alkylideneaminoxy which is unsubstituted or monosubstituted or disubstituted by alkoxy, alkylthio or phenyl, cycloalkylideneaminoxy which is unsubstituted or monosubstituted or disubstituted by alkyl, succinyliminoxy or azolyl which is unsubstituted or monosubstituted or disubstituted by alkyl or halogen, $R^2$ and $R^3$ are each alkyl, haloalkyl, alkoxy, haloalkoxy or alkylthio, $R^4$ is hydrogen, halogen, alkyl, haloalkyl or alkoxy, and Z is nitrogen or the methine group, and their use for combating unwanted plant growth.

7 Claims, No Drawings

PYRIDINE DERIVATIVES AND THEIR USE AS HERBICIDES

The present invention relates to novel pyridine derivatives and their use for controlling undesirable plant growth.

Herbicidal picolinic acid derivatives are disclosed in EP-A-249 707.

We have found novel pyridine derivatives of the formula I

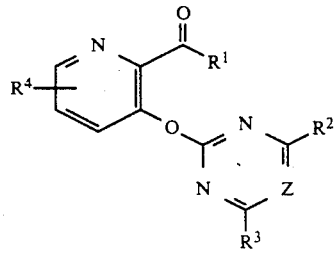

where $R^1$ is alkylideneaminoxy which is unsubstituted or monosubstituted or disubstituted by alkoxy, alkylthio or phenyl, cycloalkylideneaminoxy which is unsubstituted or monosubstituted or disubstituted by alkyl, succinyliminoxy, or azolyl which is unsubstituted or monosubstituted or disubstituted by alkyl or by halogen, $R^2$ and $R^3$ are each alkyl, haloalkyl, alkoxy, haloalkoxy or alkylthio, $R^4$ is hydrogen, halogen, alkyl, haloalkyl or alkoxy and Z is nitrogen or the methine group.

These compounds have herbicidal activities.

In formula I, the substituents $R^1$, $R^2$, $R^3$, $R^4$ and Z have the following meanings:

$R^1$ is, for example, symmetric or asymmetric $C_3$–$C_{20}$-alkylideneaminoxy, preferably $C_3$–$C_{15}$-alkylideneaminoxy, which is unsubstituted or substituted by $C_1$–$C_3$-alkylthio, $C_1$–$C_3$-alkoxy or phenyl, and unsubstituted or methyl-substituted $C_4$–$C_{12}$-, preferably $C_5$–$C_8$-cycloalkylideneaminoxy, succinyliminoxy or unsubstituted or chlorine-substituted or methyl-substituted azolyl.

$R^2$ and $R^3$ may be identical or different and are each $C_1$–$C_5$-alkyl, $C_1$–$C_5$-haloalkyl, for example $C_1$–$C_3$-chloro- or fluoroalkyl, $C_1$–$C_5$-alkoxy, $C_1$–$C_5$-haloalkoxy, for example $C_1$- or $C_2$-chloro- or fluoroalkoxy, or $C_1$–$C_4$-alkylthio.

$R^4$ is halogen, such as chlorine, fluorine or bromine, $C_1$–$C_6$-alkyl, $C_1$–$C_6$-haloalkyl, for example $C_1$- or $C_2$-chloro- or fluoroalkyl, or $C_1$–$C_5$-alkoxy.

Depending on the stated number of carbon atoms, alkyl or alkyl in an alkoxy group or in an alkylthio group is, for example, methyl, ethyl, propyl, isopropyl, butyl, sec-butyl, tert-butyl, pentyl and its isomers, hexyl and its isomers, heptyl and its isomers or octyl and its isomers. Correspondingly, the isomers are also included in the case of the higher homologs. Cycloalkylidene is, for example, cyclobutylidene, cyclopentylidene, cyclohexylidene, cycloheptylidene or cyclooctylidene. Azolyl may be imidazolyl, pyrazolyl or triazolyl.

Among the compounds of the formula I, groups which are particularly noteworthy are those in which $R^1$ is $C_5$–$C_8$-cycloalkylideneaminoxy, $C_2$–$C_{10}$-alkylideneaminoxy which is unsubstituted or substituted by methoxy, phenyl or methylthio, or imidazolyl, pyrazolyl or triazolyl, $R^2$ and $R^3$ are each $C_1$–$C_3$-alkyl, trifluoromethyl, $C_1$–$C_3$-alkoxy, difluormethoxy or $C_1$–$C_3$-alkylthio, in particular $C_1$–$C_3$-alkoxy, and $R^4$ is hydrogen, fluorine, chlorine, bromine, $C_1$–$C_4$-alkyl or $C_1$–$C_4$-alkoxy, in particular hydrogen. Particularly active compounds are those in which Z is the methine group.

The pyridine derivatives of the formula I can be obtained in a conventional manner by reacting a picolinic acid derivative of the formula II

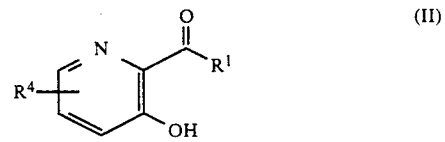

where $R^1$ is hydroxyl and $R^4$ has the meanings stated for formula I, with a heterocycle of the formula III

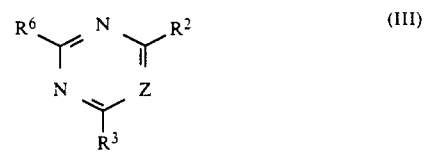

The resulting carboxylic acid substituted by a heterocyclic radical is then converted by a known method, via an activated intermediate, for example a halide or a mixed anhydride, into the pyridine derivative of the formula I. This reaction can also be carried out without activation of the carboxylic acid, in the presence of a water-eliminating agent, such as a carbodiimide.

In formula III, $R^6$ is chlorine, bromine, iodine, arylsulfonyl, alkylsulfonyl, e.g. toluenesulfonyl or methylsulfonyl, or another equivalent leaving group.

Another method for the preparation of the pyridine derivatives of the formula I is to react a picolinic acid derivative of the formula II, where $R^1$ and $R^4$ have the meanings stated for formula I, with a heterocycle of the formula III in the presence of a base.

The majority of the compounds of the formula III having a reactive substituent $R^6$ are known or can be prepared in a conventional manner without difficulties. The same applies to the picolinic acid derivatives of the formula II.

Suitable bases are alkali metal or alkaline earth metal hydrides, such as NaH or CaH$_2$, alkali metal hydroxides, such as NaOH or KOH, alkali metal alcoholates, such as potassium tert-butylate, alkali metal carbonates, such as Na$_2$CO$_3$ or K$_2$CO$_3$, alkali metal amides, such as NaNH$_2$ or lithium diisopropylamide, or tertiary amines. When an inorganic base is used, a phase-transfer catalyst can be added if this increases the conversion. The amount of base is advantageously from 1 to 20, preferably from 1 to 3, moles per mole of picolinic acid derivative II, depending on the base used.

PREPARATION EXAMPLE

General method for the preparation of aromatic carboxylic acid oxime esters of the formula I:

6.4 millimoles of the potassium salt of the particular 3-(4,6-dimethoxypyrimidin-2-yl)-oxypicolinic acid in 40 ml of dimethoxyethane are initially taken and cooled to 0° C., and 7.0 millimoles of oxalyl chloride are added. The mixture is stirred for 1 h at 0° C., after which about 30% of the solvent is evaporated under reduced pressure. 7.6 millimoles of the particular oxime and 6.4 millimoles of pyridine are then added and stirring is continued overnight at room temperature. The mixture is poured into dilute acetic acid and extracted with ethyl acetate, and the organic phase is washed with dilute acetic acid. The organic phase is dried over sodium sulfate and evaporated down under reduced pressure. The remaining substance can be further purified, for example, by chromatography over silica gel or by recrystallization from a conventional solvent.

The compounds of the formula I can be prepared by this method by selecting appropriate starting materials. Examples of pyridine derivatives of the formula I are shown in Table 1.

N,N-dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

TABLE 1

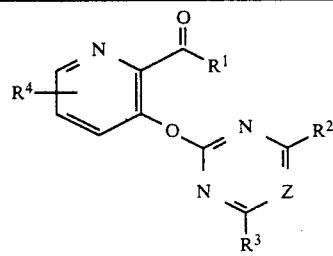

(I)

| | $R^1$ | $R^2$ | $R^3$ | $R^4$ | Z | [°C.]/δ:$^1$H-NMR [ppm] |
|---|---|---|---|---|---|---|
| 1 | 2-propaniminoxy | $OCH_3$ | $OCH_3$ | H | CH | 124–125 |
| 2 | cyclohexaniminoxy | $OCH_3$ | $OCH_3$ | H | CH | 104–109 |
| 3 | 2-methylcylcohexaniminoxy | $OCH_3$ | $OCH_3$ | H | CH | |
| 4 | 2-propaniminoxy | $OCH_3$ | $OCH_3$ | H | N | |
| 5 | 2-propaniminoxy | $SCH_3$ | $SCH_3$ | H | N | |
| 6 | 1-methoxipropan-2-iminoxy | $OCH_3$ | $OCH_3$ | H | CH | 76–78 |
| 7 | 3-methylthiobutan-2-iminoxy | $OCH_3$ | $OCH_3$ | H | CH | 91–94 |
| 8 | 1-phenylethan-1-iminoxy | $OCH_3$ | $OCH_3$ | H | CH | 112–114 |
| 9 | 2-dodecaniminoxy | $OCH_3$ | $OCH_3$ | H | CH | |
| 10 | 2-methylhexan-3-iminoxy | $OCH_3$ | $OCH_3$ | H | CH | 98–99 |
| 11 | 1-imidazolyl | $OCH_3$ | $OCH_3$ | H | CH | |
| 12 | 1-([1,2,4]-triazolyl) | $OCH_3$ | $OCH_3$ | H | CH | |
| 13 | 1-pyrazolyl | $OCH_3$ | $OCH_3$ | H | CH | |
| 14 | 2-propaniminoxy | $CH_3$ | $OCH_3$ | H | CH | |
| 15 | 2-propaniminoxy | $CF_3$ | $OCH_3$ | H | CH | |
| 16 | 2-propaniminoxy | $OCHF_2$ | $OCHF_2$ | H | CH | |
| 17 | 2-propaniminoxy | $OCH_3$ | $OCH_3$ | 6-$CH_3$ | CH | |
| 18 | 3-dodecaniminoxy | $OCH_3$ | $OCH_3$ | H | CH | 0.08–1.60 (m; 20H); 2.26–2.50 (m; 4H); 3.80 (s; 6H); 5.77 (s; 1H) |

The pyridine derivatives of the formula I, and agents containing them, are herbicidally active.

The compounds of the formula I, and herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, cyclohexanol, cyclohexanone, chlorobenzene, isophorone, etc., and strongly polar solvents such as Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, alkali metal and alkaline earth metal salts of dibutylnaphthalenesulfonic acid, lauryl ether sulfate, fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient.

Examples of formulations are as follows:

I. 90 parts by weight of compound no. 5 is mixed with 10 parts by weight of N-methyl-alpha-pyrrolidone. A mixture is obtained which is suitable for application in the form of very fine drops.

II. 20 parts by weight of compound no. 1 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 2 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 4 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 14 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 16 is intimately mixed with 97 parts by weight of particulate kaolin. A dust is obtained containing 3% by weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 5 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 3.0, preferably 0.01 to 1.0, kg of active ingredient per hectare.

In view of the number of application methods possible, the compounds according to the invention, or agents containing them, may be used in a further large number of crops for removing unwanted plants.

To increase the spectrum of action and to achieve synergistic effects, the pyridine derivatives of the formula I may be mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, (hetero)-aryloxypropionic acids and derivatives thereof, etc.

It may also be useful to apply the pyridine derivatives of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

EXAMPLES DEMONSTRATING BIOLOGICAL ACTION

The influence of various representatives of the pyridine derivatives of the formula I on the growth of unwanted and crop plants is demonstrated in the following greenhouse experiments:

The vessels employed were plastic flowerpots having a volume of 300 cm$^3$ and filled with a sandy loam containing about 3.0% humus. The seeds of the test plants were sown separately, according to species.

For the postemergence treatment, either plants sown directly in the pots and grown there were used, or plants which were cultivated separately as seedlings and were transplanted to the vessels a few days before treatment.

The plants used in the experiments were *Abutilon theophrasti, Amaranthus retroflexus, Chenopodium album, Malva neglecta, Solanum nigrum* and *Stellaria media.*

Depending on growth form, the plants were grown to a height of 3 to 15 cm before being treated with the active ingredients, which were suspended or emulsified in water and sprayed through finely distributing nozzles. The application rate for postemergence treatment was 0.06 kg/ha.

The pots were set up in the greenhouse, species from warmer climates in warmer areas (20° to 35° C.) and species from moderate climates at 10° to 20° C. The experiments were run for from 2 to 4 weeks. During this time the plants were tended and their reactions to the various treatments assessed.

The assessment scale was 0 to 100, 100 denoting nonemergence or complete destruction of at least the visible plant parts, and 0 denoting no damage or normal growth.

Postemergence application of, for instance, active ingredients nos. 1 and 2, gave good control of unwanted broadleaved plants.

We claim:

1. A pyridine derivative of the formula I 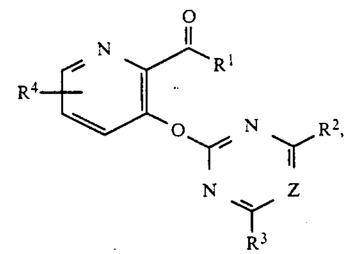 (I)

where $R^1$ is $C_3$–$C_{20}$-alkylideneaminoxy which is unsubstituted or monsubstituted or disubstituted by $C_1$–$C_3$-alkoxy, $C_1$–$C_3$-alkylthio or phenyl, $C_3$–$C_{15}$-cycloalkylideneaminoxy which is unsubstituted or monosubstituted or disubstituted by methyl, $R^2$ and $R^3$ are each $C_1$–$C_5$-alkyl, $C_1$–$C_5$-haloalkyl, $C_1$–$C_5$-alkoxy or $C_1$–$C_4$-alkylthio, $R^4$ is hydrogen, halogen, $C_1$–$C_6$-alkyl, $C_1$–$C_6$-haloalkyl, or $C_1$–$C_5$-alkoxy, and Z is nitrogen or the methine group.

2. A pyridine derivative of the formula I as set forth in claim 1, where Z is the methine group.

3. A pyridine derivative of the formula I as set forth in claim 1, where $R^1$ is 2-propaniminoxy, $R^2$ is methoxy, $R^3$ is methoxy, $R^4$ is hydrogen and Z is the methine group.

4. A herbicidal composition consisting essentially of inert additives and a herbicidally effective amount of a pyridine derivative of the formula I as set forth in claim 1.

5. A method of combating the growth of unwanted plants, wherein a herbicidally effective amount of a pyridine derivative of the formula I as set forth in claim 1 is allowed to act on the plants or their habitat.

6. A method as set forth in claim 5, wherein the amount of pyridine derivative of the formula I is from 0.001 to 3 kg/ha.

7. A method of combating the growth of unwanted plants which comprises applying to the plants or their habitat a herbicidally effective amount of a pyridine derivative of the formula I as defined in claim 3.

* * * * *